United States Patent

Ichinohe et al.

[11] Patent Number: 6,140,524
[45] Date of Patent: Oct. 31, 2000

[54] METHOD FOR PREPARING A SHORT-CHAIN POLYSULFIDE SILANE MIXTURE

[75] Inventors: Shoji Ichinohe; Hideyoshi Yanagisawa, both of Usui-gun, Japan

[73] Assignee: Shin-Etsu Chemical Co., Ltd., Japan

[21] Appl. No.: 09/201,819

[22] Filed: Dec. 1, 1998

[30] Foreign Application Priority Data

Dec. 1, 1997 [JP] Japan .................................. 9-345897

[51] Int. Cl.$^7$ ...................................................... C07F 7/08
[52] U.S. Cl. ............................................... 556/427
[58] Field of Search ............................................. 556/427

[56] References Cited

U.S. PATENT DOCUMENTS

| | | |
|---|---|---|
| 3,842,111 | 10/1974 | Meyer-Simon et al. . |
| 3,873,489 | 3/1975 | Thurn et al. . |
| 3,997,356 | 12/1976 | Thurn et al. . |
| 4,076,550 | 2/1978 | Thurn et al. . |
| 4,507,490 | 3/1985 | Panster et al. ........................... 556/427 |
| 5,399,739 | 3/1995 | French et al. ........................... 556/427 |
| 5,405,985 | 4/1995 | Parker et al. ........................... 556/427 |
| 5,466,848 | 11/1995 | Childress . |
| 5,468,893 | 11/1995 | Parker et al. ........................... 556/427 |
| 5,489,701 | 2/1996 | Childress et al. ........................ 556/427 |
| 5,580,919 | 12/1996 | Agostini et al. . |
| 5,596,116 | 1/1997 | Childress et al. ........................ 556/427 |
| 5,663,396 | 9/1997 | Musleve et al. ......................... 556/427 |
| 5,674,932 | 10/1997 | Agostini et al. . |
| 5,770,754 | 6/1998 | Scholl ..................................... 556/427 |
| 5,859,275 | 1/1999 | Munzenberg et al. ................... 556/427 |
| 5,892,085 | 4/1999 | Munzenberg et al. ................... 556/427 |

FOREIGN PATENT DOCUMENTS

| | | |
|---|---|---|
| 0 848 006 | 6/1998 | European Pat. Off. . |
| 2141159 | 3/1973 | Germany . |
| 48-29726 | 4/1973 | Japan . |
| 7-228588 | 8/1995 | Japan . |
| 8-259739 | 10/1996 | Japan . |

OTHER PUBLICATIONS

Patent Abstract of Japan, Publication No. 07 228588A, Aug. 29, 1995.
European Search Report.
Patent Abstract of Japan, Publication No. 07228588A, Aug. 29, 1995.

*Primary Examiner*—Paul F. Shaver
*Attorney, Agent, or Firm*—Millen, White, Zelane & Branigan, P.C.

[57] ABSTRACT

A mixture of short-chain polysulfide silanes of the formula: $(RO)_3SiC_3H_6S_nC_3H_6Si(OR)_3$ wherein R is methyl or ethyl and n is a positive number having a distribution whose average falls in the range: $2.2 \leq n \leq 2.8$ is prepared by reacting metal polysulfides, typically $Na_2S_n$ with a halogenopropyltrialkoxysilane of the formula: $(RO)_3SiC_3H_6X$ wherein X is halogen.

17 Claims, No Drawings

METHOD FOR PREPARING A SHORT-CHAIN POLYSULFIDE SILANE MIXTURE

BACKGROUND OF THE INVENTION

1. Field of the Invention

This invention relates to a method for preparing a mixture of short-chain polysulfide silanes for use in silica-loaded tire compounds.

2. Prior Art

In prior art silica-loaded tire compounds, bis(triethoxysilylpropyl)tetrasulfide is often used as a coupling agent for forming a bond between rubber and silica. This compound, however, has the problem that when milled with rubber and silica at elevated temperatures, it causes the blend to increase its Mooney viscosity to such an extent as to restrain subsequent working.

Then JP-A 259739/1996 discloses a method for improving the workability of a rubber compound loaded with silica and bis(triethoxysilylpropyl)tetrasulfide. When bis(triethoxysilylpropyl)tetrasulfide is used alone, however, workability is improved at the sacrifice of low fuel consumption characteristic of the silica-loaded tires.

We thus paid attention to polysulfide silane mixtures and discovered that a good compromise is made between low fuel consumption and workability when a mixture of polysulfide silanes represented by the following general formula (1) is used.

(1)

Herein n is a positive number having a distribution whose average is in the range: $2.2 \leq n \leq 2.8$. and R is methyl or ethyl.

With respect to the preparation of a mixture of polysulfide silanes of formula (1), JP-A 228588/1995 discloses a method involving reacting $Na_2S$ with sulfur to produce polysulfides and continuously reacting the reaction product with a halogenoalkoxysilane without isolating the polysulfides.

This preparation method, however, has some problems. Because of a substantial variation between lots, the distribution of n in formula (1) sometimes deviates from the desired range. The reaction with the halogenoalkoxysilane is effected in a large amount of solvent, which leads to a low pot yield.

With respect to reaction of sodium polysulfide with halogenoalkoxysilane, JP-A 29726/1973 discloses reaction between $Na_2S_4$ or $Na_2S_2$ alone and a halogenoalkoxysilane. This patent pertains to the reaction of a single compound, sodium tetrasulfide or sodium disulfide, but teaches nowhere the reaction of polysulfides having a distribution ($2.2 \leq n \leq 2.8$) with a halogenoalkoxysilane.

Therefore, an object of the invention is to provide a novel and improved method for preparing a mixture of short-chain polysulfides of formula (1) in a simple, efficient and steady manner in high yields.

SUMMARY OF THE INVENTION

To achieve the above object, we attempted to prepare a mixture of short-chain polysulfide silanes as follows. A metal sulfide is reacted with sulfur in a solvent, for example, to form polysulfides, which are adjusted to a mixture of polysulfides represented by formula (2) or (3):

(2)

(3)

wherein M is an alkali metal or ammonium, N is an alkaline earth metal or zinc, and n is a positive number having a distribution whose average falls in the range: $2.2 \leq n \leq 2.8$. These polysulfides are reacted with a halogenopropyltrialkoxysilane of the following general formula (4):

(4)

wherein X is a halogen atom and R is methyl or ethyl. Then, a mixture of short-chain polysulfide silanes represented by the following general formula (1):

(1)

wherein n and R are as defined above is produced in an efficient and steady manner in high yields. Because of its distribution, the short-chain polysulfide silane mixture is effective for achieving both low fuel consumption and workability when blended in silica-loaded rubber compounds.

Accordingly, the present invention provides a method for preparing a mixture of short-chain polysulfide silanes of formula (1), comprising the step of reacting polysulfides of formula (2) or (3) with a halogenopropyl-trialkoxysilane of formula (4).

Since the polysulfide silane mixture obtained by the inventive method is not a single compound (wherein n is an integer), inexpensive manufacture is possible. The invention is advantageous when it is desired to control the distribution of a short-chain polysulfide silane mixture. When a mixture of polysulfides of formula (2) or (3) is isolated and adjusted, the distribution of this polysulfide mixture can be controlled. Then the distribution of a short-chain polysulfide silane mixture can be easily controlled, as compared with the case wherein the polysulfide mixture is not isolated. In the prior art where the polysulfide mixture is not isolated, a large amount of solvent such as alcohol must be used in order to dissolve sulfides such as sodium sulfide ($Na_2S$) in the system. Since polysulfides such as sodium polysulfides wherein n is in the range of 2.2 to 2.8 are more dispersible in the solvent than the sulfides such as sodium sulfide ($Na_2S$), the amount of the solvent used for reaction with halogenopropyltrialkoxysilane can be reduced, leading to an improved pot yield.

It might occur to those skilled in the art to produce a mixture of short-chain polysulfide silanes by desulfurizing tetrasulfide silane with sodium cyanide. As compared with the desulfurizing method, the method of the invention ensures low cost and safety in preparing a mixture of short-chain polysulfide silanes.

DETAILED DESCRIPTION OF THE INVENTION

In the method for preparing a mixture of short-chain polysulfide silanes according to the invention, a mixture of metal polysulfides of formula (2) or (3) is first isolated and adjusted so that free sulfur is absent and the average of distribution of n may fall in the range of 2.2 to 2.8. The metal polysulfide mixture is then reacted with a halogenopropyltrialkoxysilane of formula (4) in a solventless system or in a solvent, thereby producing a mixture of short-chain polysulfide silanes of formula (1).

(1)

(2)

(3)

(4)

In formulas (1) to (4), n is a positive number having a distribution whose average falls in the range: $2.2 \leq n \leq 2.8$, R is methyl or ethyl, M is an alkali metal or ammonium, N is an alkaline earth metal or zinc, and X is a halogen atom.

Examples of the metal polysulfides represented by formulas (2) and (3) include $Na_2S_n$, $K_2S_n$, $Li_2S_n$, $(NH_4)_2S_n$, $CaS_n$, $MgS_n$, and $ZnS_n$, with $Na_2S_n$ being especially preferred.

The manner of preparing metal polysulfides is not critical. In one example, they can be prepared by reacting a metal sulfide represented by $M_2S$ or NS wherein M and N are as defined above with sulfur in a solvent. The molar ratio of metal sulfide to sulfur is determined as appropriate. When sodium sulfide is used, for example, the desired mixture of sodium polysulfides can be obtained by reacting 1 mol of sodium sulfide with 1.2 to 1.8 mol of sulfur.

In this reaction, the solvent permitting the metal sulfide to be partially dissolved in the reaction system is advantageously used. Illustrative examples of the solvent include aliphatic solvents such as pentane and hexane, aromatic solvents such as benzene, toluene, and xylene, ethers such as diethyl ether and dibenzyl ether, esters, and ketones. The most advantageous solvents are alcohols such as methanol, ethanol, propanol, butanol, benzyl alcohol, and phenol, with methanol and ethanol being especially advantageous.

The reaction temperature may range from room temperature to 150° C., more preferably from 60 to 100° C. Solvent reflux conditions, especially ethanol reflux conditions are appropriate. Unless the metal sulfide is partially dissolved in the reaction system, the reaction between sulfur and metal sulfide does not proceed to a full extent, leaving some sulfur unreacted and failing to produce a mixture of metal polysulfides having the desired distribution.

At the end of reaction, the solvent used is distilled off in vacuum, leaving the mixture of metal polysulfides. The metal polysulfide mixture thus obtained can be isolated and adjusted in distribution by a sublimation technique utilizing a difference in sublimation temperature.

After the distribution adjustment, the metal polysulfide mixture is reacted with a halogenopropyl-trialkoxysilane of formula (4):

$$(RO)_3SiC_3H_6X \qquad (4)$$

wherein X is a halogen atom such as Cl, Br or I, preferably Cl or Br, and R is methyl or ethyl. Examples of the compound of formula (4) include $ClC_3H_6Si(OC_2H_5)_3$, $ClC_3H_6Si(OCH_3)_3$, and $BrC_3H_6Si(OC_2H_5)_3$.

When the metal polysulfide mixture is reacted with the halogenopropyltrialkoxysilane, a solvent may or may not be used. When used, the solvent permitting the metal sulfide to be partially dissolved in the reaction system is advantageous. Examples of the solvent are as described above. Illustrative examples of the solvent include aliphatic solvents such as pentane and hexane, aromatic solvents such as benzene, toluene, and xylene, ethers such as diethyl ether and dibenzyl ether, esters, and ketones. The most advantageous solvents are alcohols such as methanol, ethanol, propanol, butanol, benzyl alcohol, and phenol, with methanol and ethanol being especially advantageous.

The reaction temperature may range from room temperature to 150° C., more preferably from 60 to 100° C. Solvent reflux conditions, especially ethanol reflux conditions are appropriate. The reaction time is usually 1 to 20 hours although reaction may proceed to completion within 1 to 5 hours under ethanol reflux conditions.

After the completion of reaction, the solvent is distilled off under vacuum and the salt formed is filtered off, obtaining the desired mixture of short-chain polysulfide silanes of formula (1) in high yields.

With respect to the short-chain polysulfide silane mixture of formula (1), if n is less than 2.2, tires having the polysulfide silane mixture blended therein are unsatisfactory in fuel consumption reduction. If n is more than 2.8, the rubber milled together with the polysulfide silane mixture at elevated temperature becomes poorly workable. The more preferred range of n is from 2.3 to 2.7, within which the best compromise between low fuel consumption and workability is found.

There has been described a method for preparing a mixture of short-chain polysulfides of formula (1) in a simple and steady manner in high yields.

EXAMPLE

Examples of the invention are given below by way of illustration and not by way of limitation.

Example 1

Anhydrous sodium sulfide ($Na_2S$), 1 mol, was reacted with 1.5 mol of sulfur in a nitrogen gas atmosphere to form a mixture of sodium polysulfides, which was adjusted to an average composition: $Na_2S_{2.5}$, characterized by the absence of free sulfur and a sulfur content of 63% by weight. A 2-liter flask was charged with 126 g (1 mol) of the sodium polysulfide mixture and 130 g of ethanol, to which 481 g (2 mol) of chloropropyltriethoxysilane was added dropwise under ethanol reflux conditions. After the reaction mixture was ripened for 5 hours, the ethanol was distilled off and the sodium chloride formed was filtered off, obtaining 470 g of polysulfide silanes having an average sulfide chain of 2.5 (yield 96%). On supercritical chromatographic analysis, this was found to be a polysulfide silane mixture of the following composition.

| | |
|---|---|
| disulfide silane | 56% by weight |
| trisulfide silane | 31% by weight |
| tetrasulfide silane | 10% by weight |
| penta and poly-sulfide silanes | 3% by weight |

Example 2

Reaction was carried out as in Example 1 except that 116 g (1 mol) of $Na_2S_{2.2}$ (characterized by the absence of free sulfur and a sulfur content of 60% by weight) prepared in the same manner as $Na_2S_{2.5}$ in Example 1 was used. There was obtained 450 g of polysulfide silanes having an average sulfide chain of 2.2 (yield 94%). This mixture had the following composition.

| | |
|---|---|
| disulfide silane | 78% by weight |
| trisulfide silane | 17% by weight |
| tetrasulfide silane | 5% by weight |

Comparative Example 1

A 2-liter flask was charged with 78 g (1 mol) of $Na_2S$ instead of $Na_2S_{2.5}$ in Example 1, 48 g (1.5 mol) of sulfur, and 130 g of ethanol. Reaction was effected for 5 hours under ethanol reflux conditions. The subsequent procedure was the same as in Example 1, yielding 460 g of a product.

This product had the following composition indicating the presence of residual sulfur.

| monosulfide silane | 48% by weight |
|---|---|
| disulfide silane | 45% by weight |
| sulfur | 7% by weight |

Comparative Examples 2–4

In accordance with the method of JP-A 259739/1996, $(C_2H_5O)_3SiC_3H_6S_2C_3H_6Si(OC_2H_5)_3$ was synthesized by oxidizing $(C_2H_5O)_3SiC_3H_6SH$ in the presence of manganese dioxide (Comparative Example 2).

Single compounds $Na_2S_3$ and $Na_2S_4$ each were purified by a sublimation technique and reacted with chloropropyltriethoxysilane to produce single compounds: $(C_2H_5O)_3SiC_3H_6S_3C_3H_6Si(OC_2H_5)_3$ (Comparative Example 3) and $(C_2H_5O)_3SiC_3H_6S_4C_3H_6Si(OC_2H_5)_3$ (Comparative Example 4).

The polysulfide silanes of Examples 1 and 2 and Comparative Examples 2–4 were examined for a balance of low fuel consumption and workability by the following test. The results are shown in Table 1.

The low fuel consumption was rated in terms of hysteresis loss (or heat generation). A rubber compound obtained in the workability test was measured for tanδ by a viscoelasticity spectrometer (Iwamoto Mfg. K.K.). A sample with low tanδ was rated OK, and a sample with greater tanδ rated NG.

In the workability test, a rubber compound was prepared by-milling at 150° C. 100 parts by weight of styrene-butadiene rubber, 60 parts by weight of silica (Nipsil AQ by Nippon Silica K.K.), and 6 parts by weight of the polysulfide silane and measured for Mooney viscosity ($ML_{1+4}$) at 130° C. A rubber compound which experienced little increase of Mooney viscosity and remained well workable was rated "Good", a rubber compound which experienced an increase of Mooney viscosity and remained fairly workable was rated "Fair", and a rubber compound which experienced a substantial increase of Mooney viscosity (partially gelled) and became difficult to work was rated "Poor".

TABLE 1

| | Low fuel consumption | Workability |
|---|---|---|
| Example 1 | OK | Good |
| Example 2 | OK | Good |
| Comparative Example 2 | NG | Good |
| Comparative Example 3 | OK | Fair |
| Comparative Example 4 | OK | Poor |

Japanese Patent Application No. 345897/1997 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. A method for preparing a mixture of short-chain polysulfide silanes represented by formula (1):

$$(RO)_3SiC_3H_6S_nC_3H_6Si(OR)_3 \qquad (1)$$

wherein R is methyl or ethyl and n is a positive number having a distribution, the average of the distribution being $2.2 \leq n \leq 2.8$, said method comprising the step of reacting polysulfides represented by the following general formula (2) or (3):

$$M_2S_n \qquad (2)$$

$$NS_n \qquad (3)$$

wherein M is an alkali metal or ammonium, N is an alkaline earth metal or zinc, and n is as defined above, with a halogenopropyltrialkoxysilane of the following general formula (4):

$$(RO)_3SiC_3H_6X \qquad (4)$$

wherein X is a halogen atom and R is as defined above, in an alcohol, said polysulfides of formula (2) or (3) being prepared by reacting a metal sulfide represented by $M_2S$ or NS wherein M and N are as defined above with sulfur in an alcohol, and isolating and adjusting the obtained metal polysulfide mixture so that free sulfur is absent and the average of distribution of n falls in the range of 2.2 to 2.8.

2. A method as claimed in claim 1, wherein the polysulfide is prepared at a reaction temperature of from room temperature to 150° C.

3. The method of claim 2, wherein the reaction of the metal sulfide with sulfur is effected in a solvent permitting the metal sulfide to be partially dissolved.

4. The method of claim 2 wherein after the reaction of the metal sulfide with sulfur, the obtained metal polysulfide mixture is isolated and adjusted so that free sulfur is absent and the average of distribution of n in the general formula (2) or (3) falls in the range of 2.2 to 2.8.

5. The method of claim 1, wherein the polysulfide represented by the formula (2) or (3) is $Na_2Sn$ prepared by reacting 1 mol of sodium sulfide with 1.2 to 1.8 mol of sulfur.

6. A method as claimed in claim 1, wherein the polysulfide is prepared at a reaction temperature of from 60 to 100° C.

7. A method as claimed in claim 1, wherein the polysulfide is reacted with the halogenopropyltrialkoxysilane at a temperature of from room temperature to 150° C.

8. A method as claimed in claim 1, wherein the polysulfide is reacted with the halogenopropyltrialkoxysilane at a temperature of from room temperature to 150° C.

9. A method as claimed in claim 1, wherein the polysulfide is reacted with the halogenopropyltrialkoxysilane at a temperature of from 60 to 100° C.

10. A method as claimed in claim 1, wherein the value of n is from 2.3 to 2.7.

11. A method for preparing a mixture of short-chain polysulfide silanes represented by formula (1):

$$(RO)_3SiC_3H_6S_nC_3H_6Si(OR)_3 \qquad (1)$$

wherein R is methyl or ethyl and n is a positive number having a distribution, the average of the distribution being $2.2 \leq n \leq 2.8$, said method comprising the step of reacting polysulfides represented by formula (2) or (3):

$$M_2S_n \qquad (2)$$

$$NS_n \qquad (3)$$

wherein M is an alkali metal or ammonium, N is an alkaline earth metal or zinc, and n is as defined above, with a halogenopropyltrialkoxysilane of formula (4):

$$(RO)_3SiC_3H_6X \qquad (4)$$

wherein X is a halogen atom and R is as defined above, in an alcohol, said polysulfide being prepared by reacting a metal sulfide represented by $M_2S$ or NS wherein M and N are as defined above with sulfur in an organic solvent at ambient temperature and pressure in a solvent reflux, and isolating and adjusting the obtained metal polysulfide mixture so that free sulfur is absent and the average of distribution of n falls in the range of 2.2 to 2.8.

12. A method as claimed in claim 11, wherein the organic solvent is an alcohol.

13. A method as claimed in claim 12, wherein the organic solvent is methanol or ethanol.

14. A method as claimed in claim 11, wherein the organic solvent is an aliphatic solvent, an aromatic solvent, an ether, or a ketone.

15. A method as claimed in claim 11 wherein the value of n is from 2.3 to 2.7.

16. A method as claimed in claim 11, wherein the reactions are carried out at a temperature of from room temperature to 150° C.

17. A method as claimed in claim 11, wherein the reactions are carried out at a temperature of from 60 to 100° C.

* * * * *